(12) United States Patent
Husain

(10) Patent No.: US 6,663,654 B1
(45) Date of Patent: Dec. 16, 2003

(54) FORCEPS WITH FOREIGN BODY LOCATOR

(76) Inventor: Abbas M. Husain, Robert D. Thompson & Associates, L.L.C. 420 Benigno Blvd. Unit East B, Bellamawr, NJ (US) 08031

( * ) Notice: Subject to any disclaimer, the term of this patent is extended or adjusted under 35 U.S.C. 154(b) by 95 days.

(21) Appl. No.: 10/001,678

(22) Filed: Oct. 23, 2001

(51) Int. Cl.$^7$ ............................................... A61B 17/42
(52) U.S. Cl. ..................................................... 606/205
(58) Field of Search .................... 606/205–211, 138, 606/1, 150, 171; D28/55; D24/143; 294/99.2; 433/157, 159, 162; 81/489

(56) References Cited

U.S. PATENT DOCUMENTS

| | | |
|---|---|---|
| 427,555 A | 5/1890 | Connor |
| 880,659 A | 3/1908 | Hammergren |
| 979,697 A | 12/1910 | Prankard |
| 1,119,532 A | 12/1914 | Parks |
| 1,193,987 A | 8/1916 | Burdin |
| 1,380,232 A | 5/1921 | Metcalf |
| 2,224,384 A | 12/1940 | Gratiot |
| 4,040,846 A | 8/1977 | Broemer et al. |
| 4,300,564 A | 11/1981 | Furihata |
| 4,570,613 A | 2/1986 | Alkon |
| 4,593,694 A | 6/1986 | Langenbach, Jr. |
| 5,002,323 A | 3/1991 | Idsund |
| 5,147,369 A | 9/1992 | Wagner |
| 5,358,297 A | 10/1994 | Coleman |
| 5,449,374 A | 9/1995 | Dunn et al. |
| 5,514,156 A * | 5/1996 | Schulze et al. .............. 606/205 |
| 5,569,271 A | 10/1996 | Hoel |
| 5,591,203 A | 1/1997 | Fahy |
| 5,603,724 A | 2/1997 | O'Connor |
| 5,624,454 A | 4/1997 | Palti |
| 5,792,177 A * | 8/1998 | Kaseda ....................... 606/205 |

* cited by examiner

*Primary Examiner*—Michael J. Milano
*Assistant Examiner*—(Jackie) Tan-Uyen T. Ho
(74) *Attorney, Agent, or Firm*—Thompson Becker & Bothwell, L.L.C.; Robert D. Thompson, Esq.

(57) ABSTRACT

Forceps to facilitate the removal of foreign bodies from the skin or flesh. A rigid locator, having a circular or oval shape, is mounted to one of the jaws of the forceps by way of a rigid connector such that the opening in the rigid locator is directly in line with the opening formed by the jaws of the forceps. The opening of the rigid locator is placed around the tip of the foreign body in the flesh and pressure exerted such that the rigid locator pushes the flesh away from the top of the foreign body, permitting the jaws of the forceps to close on the exposed tip of the foreign body and remove it.

2 Claims, 3 Drawing Sheets

FORCEPS WITH FOREIGN BODY LOCATOR

BACKGROUND OF THE INVENTION

1. Field of Invention

The instant invention pertains to Class 606, Surgery, Sub-Class 205, forceps.

2. Description of the Related Art

It is a common occurrence to use forceps to remove a foreign body such as a splinter which has become embedded in human or animal skin. Forceps are used by both physicians and lay persons, depending upon the seriousness of the foreign body's embedment, to remove foreign bodies such as splinters from the skin. However, difficulties are often encountered in fixing the location of the foreign body, such as a splinter, and exposing enough of the foreign body so that the tips of the jaws of the forceps can be closed around the end of the foreign body and enable the physician or lay person to extract it. The present invention provides an apparatus for locating the tip of the foreign body and pushing the skin around the tip of the foreign body down and away from that foreign body so that a sufficient portion of the foreign body is exposed, and the exposed portion of the foreign body can be closed upon by the forceps and the foreign body extracted from the skin. The prior art includes conventional forceps and tweezers with modifications such as that disclosed in Langenblach, Jr. U.S. Pat. No. 4,593,694 which discloses tweezers with legs which flare outwardly at their free ends to form broad flat feet for contacting the skin, pushing it away and enabling the foreign body to be grasped between the opposing inner surfaces of the jaws. However, none of the known prior art discloses either forceps or tweezers with a rigidly mounted apparatus to push the skin away from the embedded splinter and enable the jaws of the forceps to grasp and remove it.

BRIEF SUMMARY OF THE INVENTION

The present invention provides an apparatus for the easy location and removal of foreign bodies such as splinters from the skin. The apparatus includes forceps with a rigid locator attached to one of the jaws of the forceps. The rigid locator is attached to one of the jaws of the forceps and positioned such that it encircles the tip of the foreign body in the skin. The rigid locator is made of a non-flexible material and is affixed to one jaw of the forceps by a rigid connecting member which holds the rigid locator a fixed distance from the jaws of the forceps such that when the forceps are pushed down on the skin, the rigid locator depresses the skin around the tip of the foreign body thereby exposing the tip of the foreign body to the jaws of the forceps which can then be closed upon the tip of the foreign body and the foreign body removed. The rigid locator may be shaped as a ring or oval and is attached to either the upper or the lower jaw of the forceps by way of a short rigid connecting member. The rigid connecting member extends along the line formed by the jaw to which it is attached and connects to the ring shaped or oval shaped rigid locator which defines a plane perpendicular to the rigid connecting member. The rigid locator is placed on the skin so that it encircles the tip of the foreign body embedded in the skin. As the forceps are pressed toward the skin, the rigid locator pushes the skin away from the tip of the foreign body exposing its tip to the jaws of the forceps which can then grasp it for easy removal.

BRIEF DESCRIPTION OF SEVERAL VIEW OF THE DRAWINGS

A more complete understanding of the invention and its advantages will be apparent from the detailed description taken in conjunction with the accompanying drawings in which FIG. 1 is a side view of the forceps with circular shaped rigid locator;

DETAILED DESCRIPTION OF THE INVENTION

Figure 1:
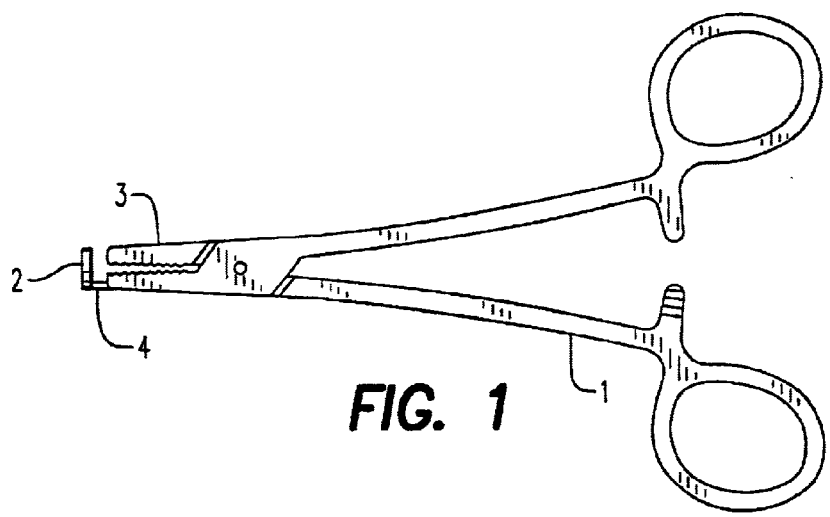
Figure 2:
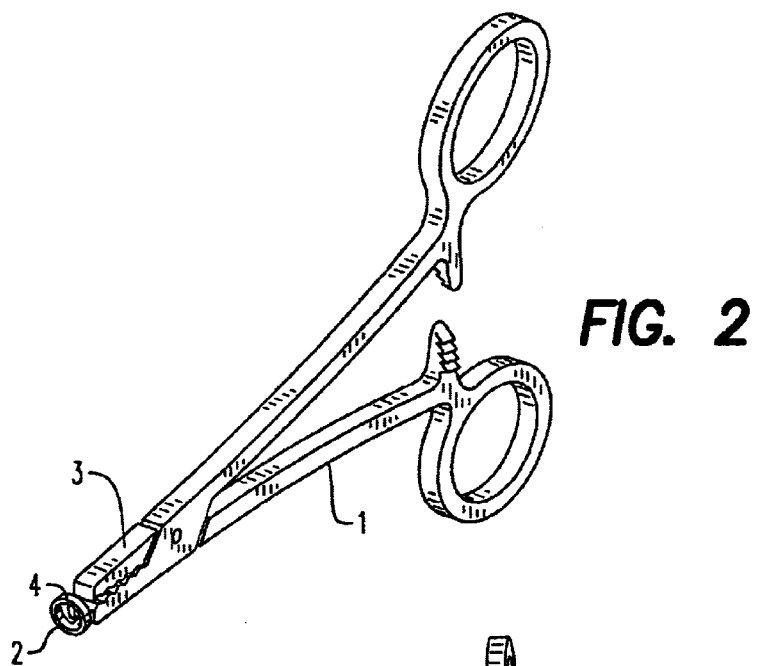
FIG. 2 is an oblique view of the forceps with circular shaped rigid locator.
Figure 3:
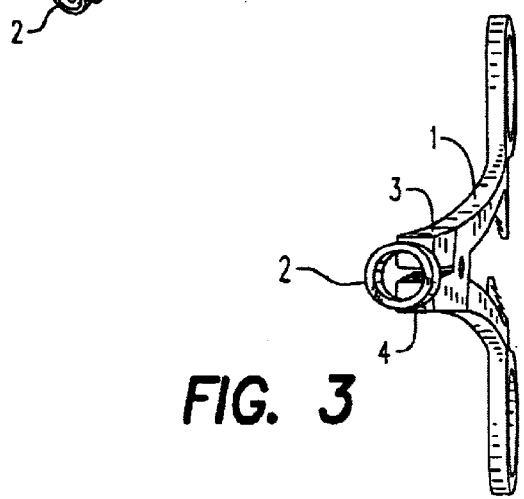
FIG. 3 is a front view of the forceps with circular shaped rigid locator.
Figure 4:
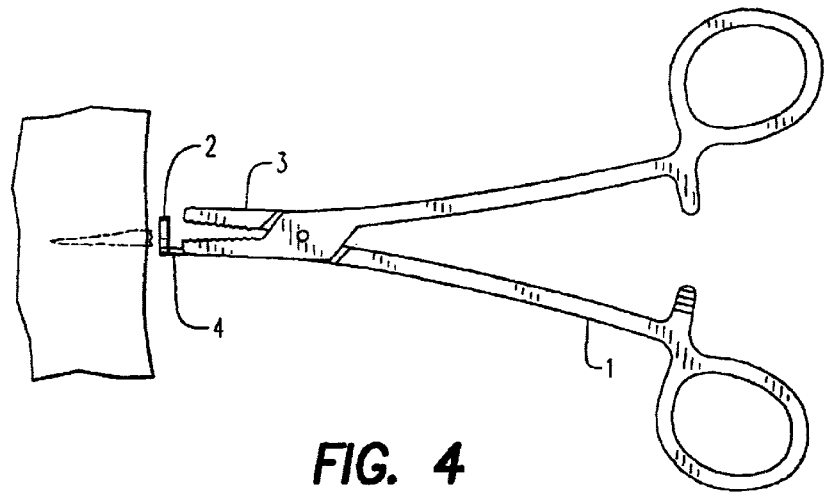
FIG. 4 and FIG. 5 are side views of the forceps with circular shaped rigid locator showing how it is used to withdraw a foreign body from the skin.
Figure 5:
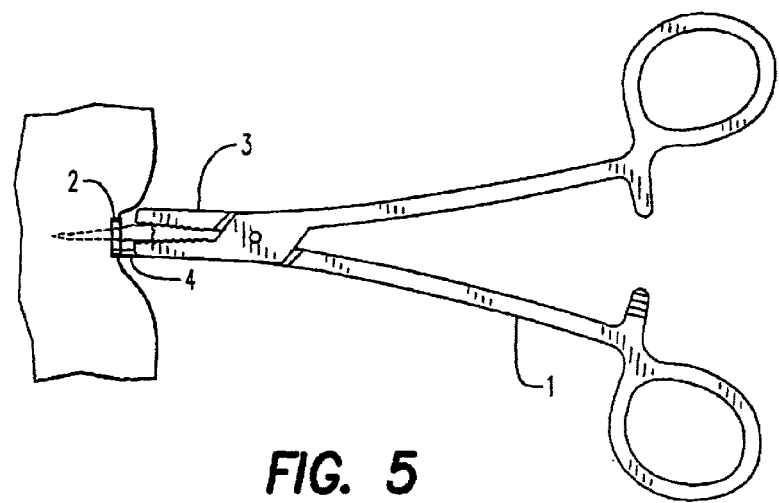
Figure 6:
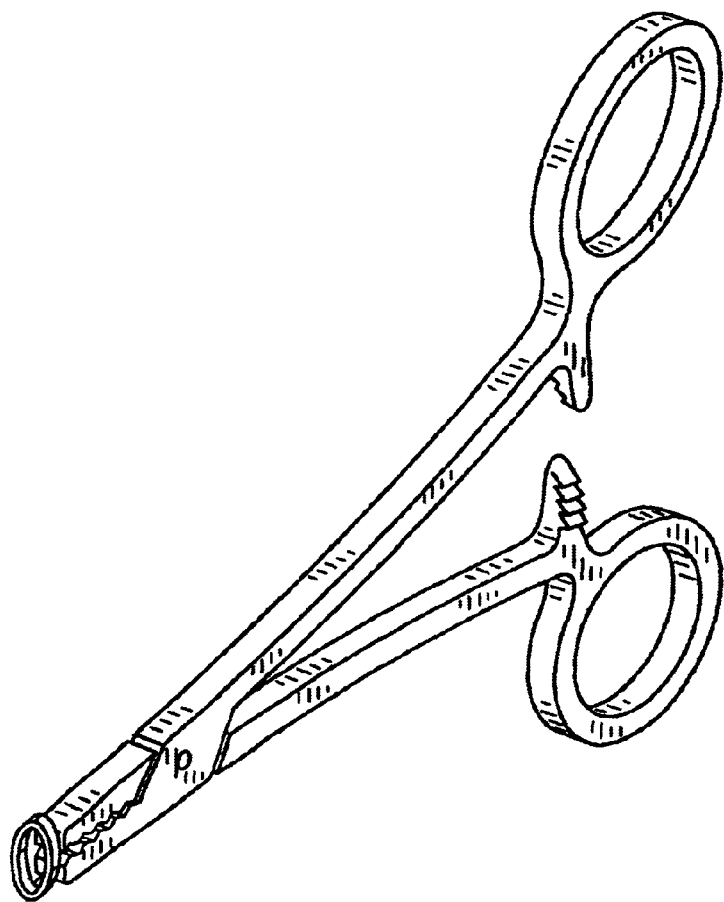
FIG. 6 is an oblique view of the forceps with oval shaped rigid locator.

Referring to FIGS. 1, 2, 3, 4, 5 and 6, the apparatus includes forceps 1, rigid connecting member 4, having two ends, one end proximal and one end distal to the jaws of the forceps 1, and rigid locator 2. The rigid locator 2, which is an enclosing device, may be formed as a circle or an oval, as shown in FIGS. 1, 2, 3, 4, 5 and 6, and is attached to either the lower or the upper jaw of the forceps 1 at the proximal end of the rigid connecting member 4. The rigid connecting member 4, attached at its distal end to the rigid locator, holds the rigid locator in place at a fixed distance in front of the jaws 3 of the forceps 1. The rigid locator 2 provides an enclosing device, the opening of which is directly in line with the opening of the forceps 1 such that the skin around the splinter or other foreign body embedded in the skin, to be grasped by the forceps, is pushed away from the sides of the splinter or other foreign body by the rigid locator 2, and the splinter or other foreign body is exposed and directed into the jaws 3 of the forceps 1. Many modifications can be made in the exemplary structure described above without exceeding the scope of the present invention. While certain embodiments of the present invention have been described in detail herein and shown in the accompanying drawings, it is obvious that minor changes may be made in the form and construction of the invention without departing from the material spirit thereof.

What is claimed is:

1. An apparatus for the removal of foreign bodies embedded in the skin of humans or animals comprising forceps having a longitudinal axis and a pair of hinged jaws on either side of the longitudinal axis, a ring shaped rigid locator having an opening which faces distally of the forceps and which defines a plane by any three points taken on the proximal edge of the opening of the rigid locator, and a rigid connecting member having two ends, one and proximal and one end distal to the jaws of the forceps; wherein the rigid connecting member is attached at its proximal end to one of the jaws of the forceps and is rigidly mounted thereto and; wherein the rigid connecting member is attached at its distal end to the proximal edge of the ring shaped rigid locator, and wherein a straight line drawn through the center of the opening of the ring shaped rigid locator and perpendicular to the plane defined by the ring shaped rigid locator, runs between the jaws of the forceps.

2. An apparatus for the removal of foreign bodies embedded in the skin of humans or animals comprising forceps having a longitudinal axis and a pair of hinged jaws on either side of the longitudinal axis, an oval shaped rigid locator having an opening which faces distally of the forceps and which defines a plane by any three points taken on the proximal edge of the opening of the rigid locator, and a rigid connecting member having two ends, one end proximal and one end distal to the jaws of the forceps wherein the rigid connecting member is attached at its proximal end to one of the jaws of the forceps and is rigidly mounted thereto, and wherein the rigid connecting member is attached at its distal end to the proximal edge of the oval shaped rigid locator arid rigidly mounted thereto, and wherein a straight line drawn through the center of the opening of the oval shaped rigid locator and perpendicular to the plane defined by the oval shaped rigid locator, runs between the jaws of the forceps.

* * * * *